US010383679B2

(12) United States Patent
Lambe (10) Patent No.: US 10,383,679 B2
(45) Date of Patent: Aug. 20, 2019

(54) COIL FOR ELECTROSURGICAL INSTRUMENT

(71) Applicant: Spiration, Inc., Redmond, WA (US)

(72) Inventor: Peter A. Lambe, Redmond, WA (US)

(73) Assignee: Spiration Inc., Redmond, WA (US)

( * ) Notice: Subject to any disclaimer, the term of this patent is extended or adjusted under 35 U.S.C. 154(b) by 284 days.

(21) Appl. No.: 15/227,563

(22) Filed: Aug. 3, 2016

(65) Prior Publication Data

US 2018/0036067 A1 Feb. 8, 2018

(51) Int. Cl.
*A61B 18/14* (2006.01)
*A61B 18/00* (2006.01)
*A61B 17/00* (2006.01)

(52) U.S. Cl.
CPC ...... *A61B 18/1477* (2013.01); *A61B 18/1492* (2013.01); *A61B 2017/00867* (2013.01); *A61B 2018/00541* (2013.01); *A61B 2018/00589* (2013.01); *A61B 2018/00982* (2013.01); *A61B 2018/1425* (2013.01); *A61B 2018/1435* (2013.01); *A61B 2018/1475* (2013.01)

(58) Field of Classification Search
CPC .... A61B 2018/1435; A61B 2018/1425; A61B 2017/00867; A61B 2018/00083; A61B 2018/00982; A61B 18/14; A61B 18/1477; A61B 2018/1405; A61B 18/1492; A61B 18/1485; A61B 2018/00589; A61B 2018/00577; A61B 2018/00541; A61B 2018/00196; A61B 18/1442; A61B 18/1445; A61B 18/1448; C07K 14/415; C12N 15/8261; Y02A 40/146; Y02E 50/17
USPC ...................................... 606/28–50
See application file for complete search history.

(56) References Cited

U.S. PATENT DOCUMENTS

| | | | |
|---|---|---|---|
| 6,018,676 A | 1/2000 | Davis et al. | |
| 6,895,282 B2 | 5/2005 | Gellman et al. | |
| 2007/0270924 A1* | 11/2007 | McCann | A61B 18/14 607/99 |
| 2009/0177114 A1 | 7/2009 | Chin et al. | |
| 2014/0276748 A1* | 9/2014 | Ku | A61B 18/18 606/33 |
| 2014/0276764 A1* | 9/2014 | Shuman | A61B 18/1477 606/34 |
| 2015/0148795 A1* | 5/2015 | Amos | A61B 18/1477 606/41 |

* cited by examiner

*Primary Examiner* — Michael F Peffley
*Assistant Examiner* — Khadijeh A Vahdat (57) ABSTRACT

An electrosurgical instrument includes a needle configured as a first electrode and a coil extending through the needle and configured as a second electrode. The coil is movable relative to the needle, and as the coil is deployed it attains a coiled configuration and a twisted configuration. After the needle and the coil are inserted into tissue and energized with an electrical energy source, the needle and the coil apply current to the tissue to coagulate the tissue.

19 Claims, 8 Drawing Sheets

COIL FOR ELECTROSURGICAL INSTRUMENT

FIELD

The present relates to an electrosurgical instrument for treating tissue.

BACKGROUND

The statements in this section merely provide background information related to the present disclosure and may not constitute prior art.

Certain electrosurgical instruments used for treating tissue generally include a guide catheter and an applicator inserted through the catheter. These electrosurgical instruments are usually inserted into a body lumen to place the distal end of the applicator at a desired location. The applicator generally includes one or more electrodes at the distal end. Such electrodes emit a radiofrequency (RF) electric current to surrounding tissue to coagulate or ablate the tissue. Monopolar electrosurgical instruments only require one electrode that interacts with a neutral electrode, which is likewise connected to the body of a patient. A bipolar electrosurgical instrument typically includes an applicator with two electrodes (a distal electrode and a proximal electrode). A RF voltage with different potentials is applied to such bipolar instruments so that a current passes from one electrode to the other electrode through the tissue, thereby heating the tissue to coagulate or ablate the tissue.

During the procedure, a sensor (e.g., ultrasound transducer, visual camera, etc.) is used at an end of a catheter to view the applicator's location relative to target tissue. However, the applicator may be difficult to see in images (i.e., ultrasound video), because the applicator fails to have sufficient echogenic properties.

SUMMARY

The present invention provides an electrosurgical instrument for treating tissue, for example, ablating or coagulating tissue.

Accordingly, pursuant to one aspect of the present invention, an electrosurgical instrument includes a needle configured as a first electrode and a coil extending through the needle and configured as a second electrode. The coil is movable relative to the needle. When the coil is deployed, the coil corkscrews into the tissue. The coil is a flat wire that is also twisted before, during or after deployment. After the needle and the coil are inserted into the target tissue and energized with an electrical energy source, the needle and the coil apply current to the target tissue thus coagulating the target tissue.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings:

FIGS. 6.1-6.3 illustrate a coil formed in accordance with the principles of the present invention.

DETAILED DESCRIPTION

The following description is merely exemplary in nature and is not intended to limit the present disclosure, application, or uses.

Figure 1:
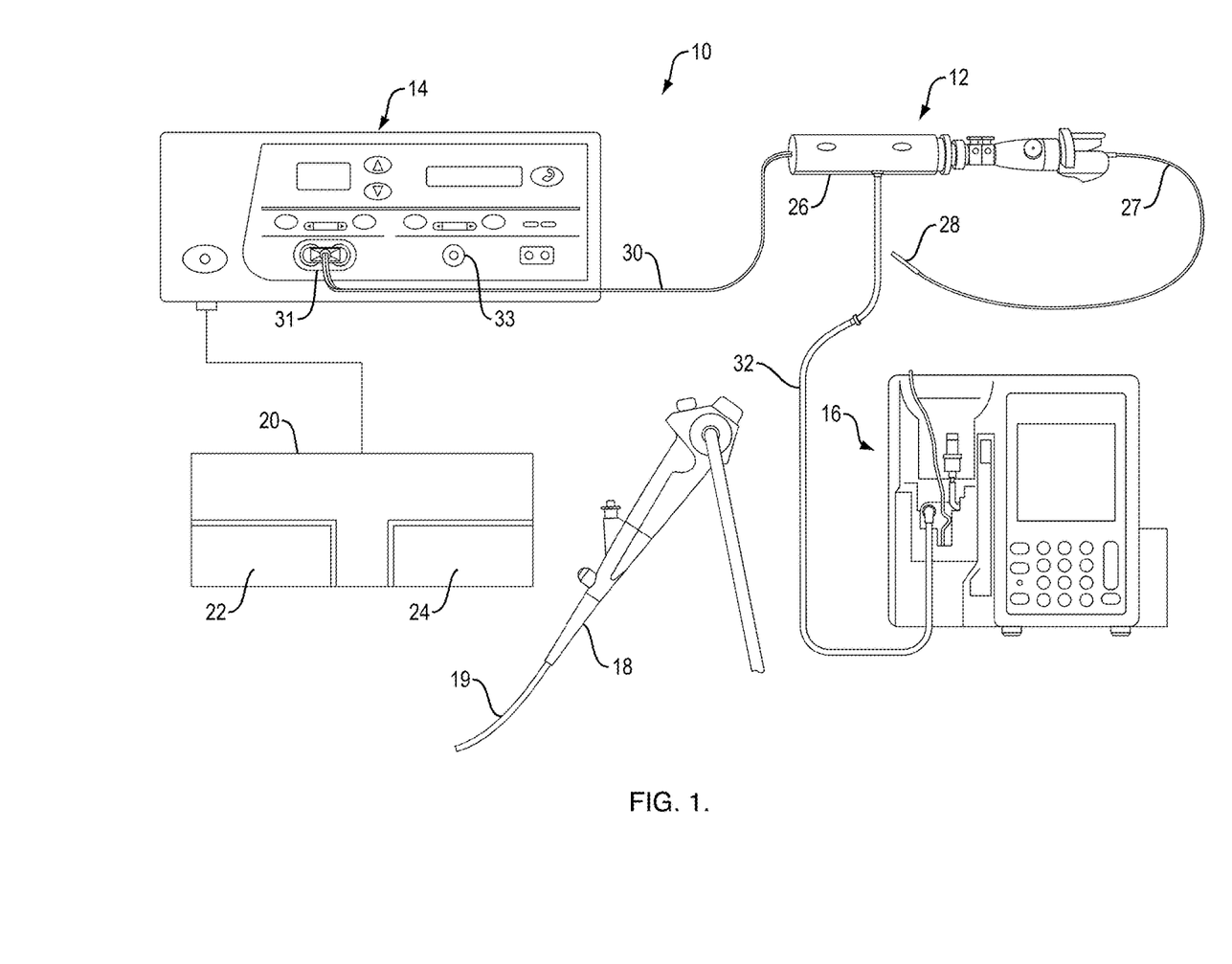
FIG. 1 illustrates an example system for treating tissue in accordance with the principles of the present invention.

FIG. 1 illustrates a system 10 for treating tissue in an anatomical region of a patient. The system 10 is a bipolar or monopolar radio frequency (RF) system for treating tissue in a patient. Specifically, the system 10 is employed for coagulation and ablation of soft tissue during percutaneous and/or endoscopic, including bronchoscopic, surgical procedures, such as, for example, partial or complete ablation of cancerous or noncancerous organ lesions.

In some arrangements, the system 10 includes an applicator 12, an electrosurgical RF generator 14, an infusion pump 16, and a bronchoscope 18. The applicator 12 electrically communicates with the generator 14 though a lead 30. The lead 30 is connected to a generator outlet 31 when the system is operated in a bipolar mode. Alternatively, the system 10 can be operated in a monopolar mode when the lead 30 is connected to an outlet 33 with an adapter as necessary. The applicator 12 is further connected to the infusion pump 16 with a tube 32 that facilitates the flow of liquid, for example saline solution, from the pump 16 to the applicator 12.

The generator 14 can be operated with the use of a foot operated unit 20 electrically connected to the generator 14. The foot operated unit 20 includes a pedal 22 that instructs the generator 14 to apply a RF potential to electrode(s) (described below) to cut or ablate tissue and a pedal 24 that instructs the generator 14 to apply a lower RF potential to the electrode(s) to coagulate tissue.

The bronchoscope 18 includes an insertion tube 19. At a distal end 36 (FIG. 2) of the insertion tube 19 is an opening 37 that is proximal to imaging camera (e.g., endobronchial ultrasound (EBUS)). The applicator 12 includes a handle 26, a needle 28 and a sheath 27. As such, in certain procedures, the needle 28 and the sheath 27 are inserted into the bronchoscope 18 so that the needle 28 exits the distal end 36 of the insertion tube 19 via the opening 37.

Figure 2:
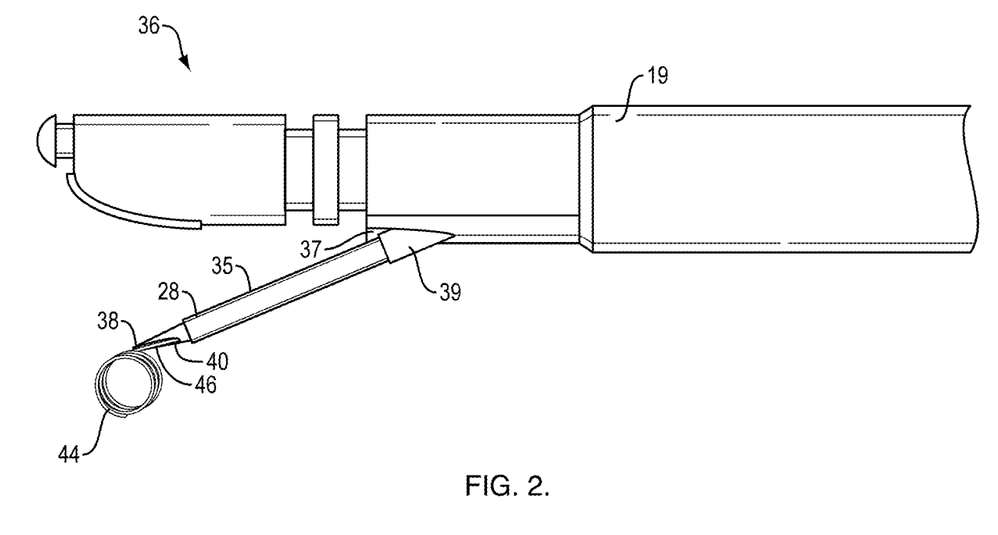
FIG. 2 illustrates a close-up view of a distal end of an insertion device of the system shown in FIG. 1.

Referring also to FIG. 2, the applicator 12 further includes a coil 44 that extends through the sheath 27 and the needle 28 and exits an opening 40 of the needle 28. The needle 28 includes a layer of insulation 35. The layer of insulation starts at a location within the sheath 39 and extends to a position proximal to a needle tip 38. The insulation 35 keeps the covered portions of the needle 28 from generating an external electric field.

The coil 44 includes a coiled portion, non-coiled portion and a layer of insulation 46 that covers the non-coiled portion of the coil 44 to electrically isolate the coil 44 from the needle 28. The layer of insulation 46 extends to the applicator 12. Accordingly, in this arrangement, the needle 28 operates as a proximal electrode and the coil 44 operates as a distal electrode when the system 10 is operated in a bipolar mode.

The tip 38 is used for piercing tissue and may include one or more echogenic features. During the penetration of the needle 28 into tissue, only the needle 28 (that is, not the coil 44) is energized in a monopolar mode (for example, with the patient grounded to a patient pad to complete the circuit) with the generator 14 at a first power level, if a penetration force exceeds what is expected by the physician. This causes the tissue to vibrate so that it can be visualized ultrasonically. The echogenic features further enhance the ultrasonic visualization of the needle 28.

Figure 3:
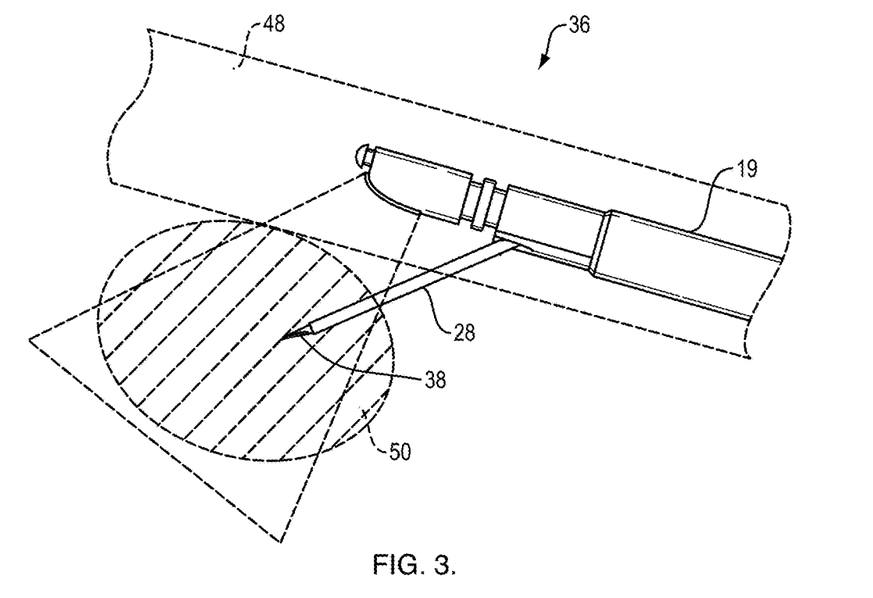
FIG. 3 illustrates the system shown in FIG. 1 during a first operational step.
Figure 4:
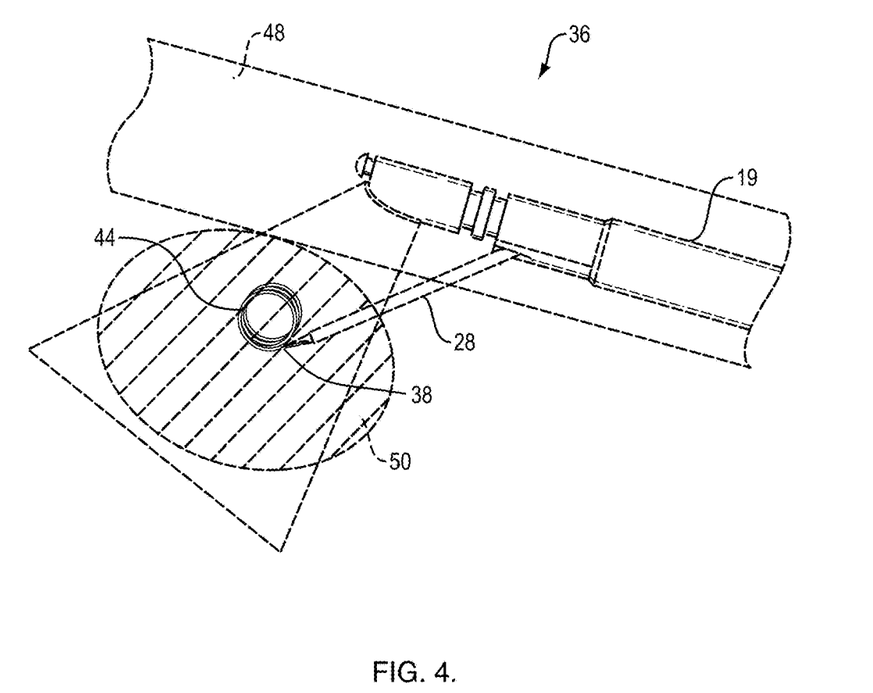
FIG. 4 illustrates the system shown in FIG. 1 during a second operational step.
Figure 5:
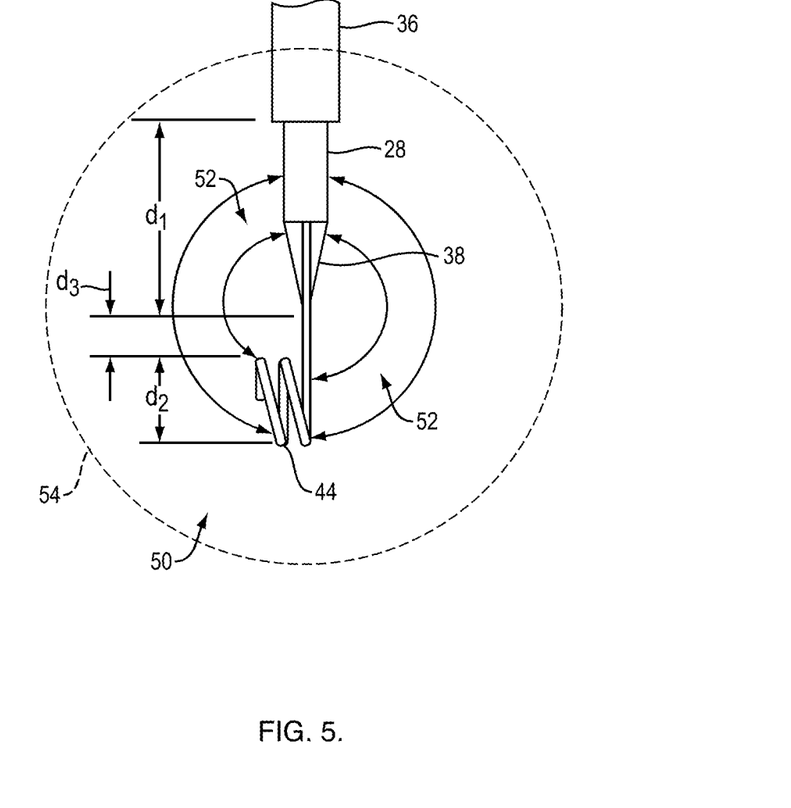
FIG. 5 illustrates side view of the system shown in FIG. 4 during a second operational step.

Referring further to FIGS. 3, 4 and 5, there is illustrated a procedure for using the system 10 during, for example, bronchoscopy. Initially, a physician advances the insertion tube 19 of the bronchoscope 18 through a passageway, for example, an airway 48, until the distal end 36 is positioned near the desired tissue 50 (e.g., tumor or lesion) to be treated. The physician then inserts the needle 28 into the insertion tube 19 and advances the needle 28 until the needle 28 exits the opening 37 at the distal end 36 and penetrates into the tissue 50 with the tip 38. While being visualized ultrasonically as described above, the needle 28 is positioned at a desired location in the tissue 50 (FIG. 3). Next the physician advances the coil 44 through the needle 28 until it exits the opening 40 to form a coil shape in the tissue 50. Either before, during or after the coil 44 advances, the coil 44 becomes twisted about its centerline. The physician continues to advance the coil 44 to the desired location (FIG. 4). Placement of the coil 44 can be visualized ultrasonically due to the twists in the coil 44. This is shown in more detail below in FIGS. 6 and 7.

As shown in FIG. 5, the coil 44 corkscrews into the tissue 50 with a diameter d2. The extent of penetration of the needle 28 (that is, the distance from the opening 37 of the distal end 36 of the insertion tube 19 to the tip 38 of the needle 28) is d1 and the distance from the coiled portion of the coil 44 to the tip 38 of the needle 28 is d3. After the coil 44 has been deployed and prior to activating the electrodes (that is, the needle 28 and the coil 44), the needle 28 is retracted proximally while the coil 44 and the insertion tube 19 (and hence the distal end 36) are held in place so that d1 decreases and d3 increases.

To energize the electrodes (the needle 28, the coil 44) for coagulating the tissue 50, the physician sets the generator 14 to a desired second power level and pushes the pedal 24 of the foot unit 20 to apply a RF potential to the electrodes. The second power level is greater than the first power level. As such, RF electrical current passes between the needle 28 and the coil 44 through the tissue 50 as indicated by the arrows 52. The level of RF electrical current is set by the physician to control the desired extent of the coagulation region 54 in the tissue 50. Note that anytime during the procedure, the physician can activate the infusion pump 16 to supply saline solution to the applicator 12 so that the saline solution flows through the needle 28 and the sheath 27 to the location of interest in the tissue 50. The saline solution is employed to cool the electrodes (the needle 28 and/or the coil 44) and to prevent dehydration of the tissue 50.

After treatment of the tissue 50 is completed, the physician turns off the generator 14, moves the needle 28 forward to the position prior to coil deployment. Then, the coil 44 is retracted into the needle 28. Then, the needle 28 and the coil 44 are retracted into the insertion tube 19 within the bronchoscope 18, and withdraws the bronchoscope 18 from the patient.

The needle 28 is made from hypotube, e.g., stainless steel. The coil 44 is a flat wire having four sides where two opposing sides have a greater width than the other opposing sides. The flat wire is made from any suitable material that enables it to be corkscrewed into tissue, such as, for example, stainless steel. In various arrangements, all or a portion of the coil 44 is made from a shape memory alloy, such as nitinol (NiTi) for either its super-elastic properties or its shape memory features. When the coil 44 is made of shape memory alloy and is implemented for its shape memory properties, the portion of the coil made of shape memory alloy has multiple configurations or states. Accordingly, when the coil 44 is in one of the configurations and then heated, the coil returns to another pre-defined configuration. Subsequently, if the coil 44 is cooled, it returns to the configuration it had when unheated.

The coil 44 is shape set to attain the coiled and/or twisted shapes when reaching a predefined temperature. The predefined temperature is the austenite finish temperature for the coil 44. See FIGS. 6.1-6.3. Because of the twisted configuration, the flat surface of the coil 44 includes a normal vector that will have different angular relationships with an ultrasound illumination device located at the distal end 36 of the insertion tube 19. In some orientations of the flat surface, the normal vector will be perpendicular or nearly perpendicular to an ultrasound signal produced by the ultrasound illumination device, thus producing a significant ultrasound feedback. See FIG. 7.

Figure 7:
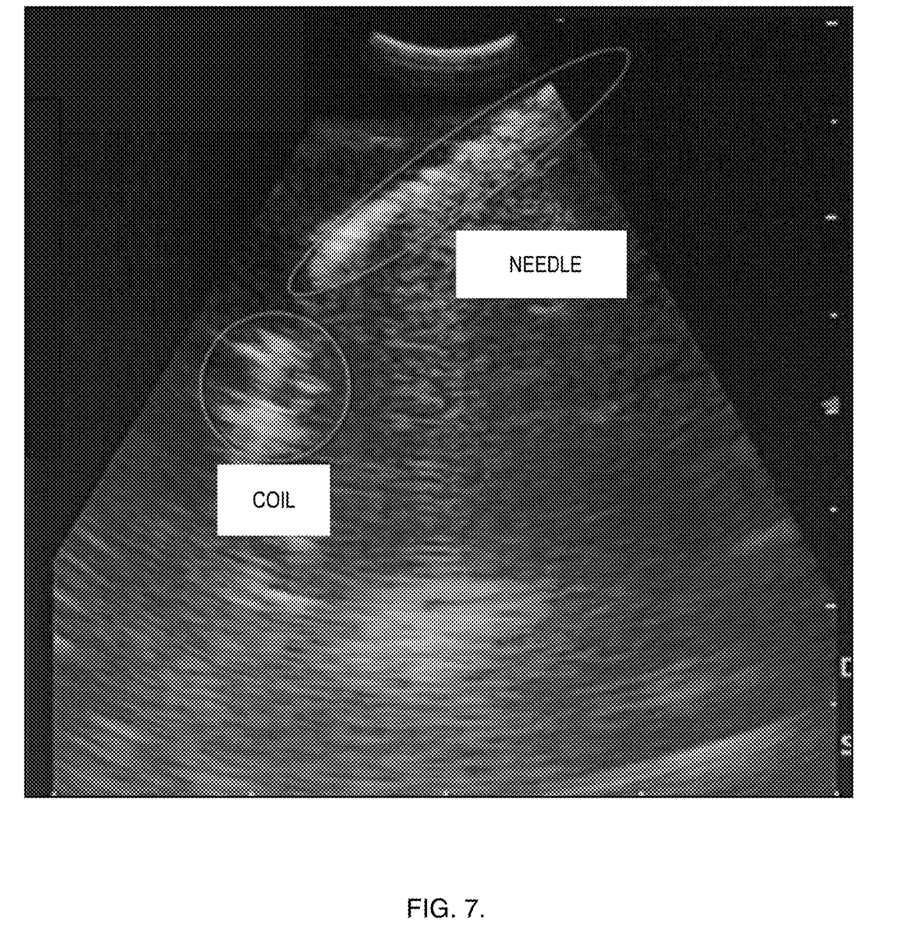
FIG. 7 illustrates an example ultrasound image of the needle and coil, shown in FIGS. 6.1-6.3.
Figure 61:
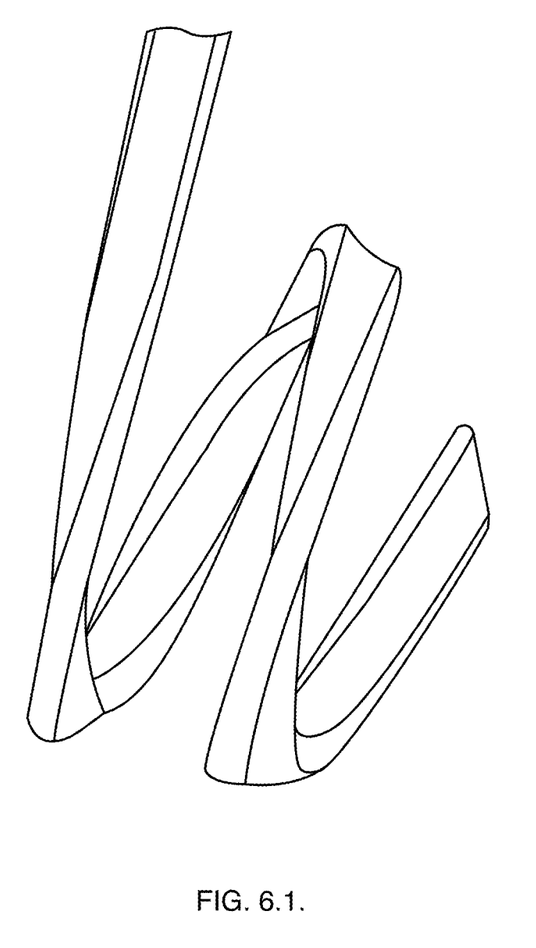
Figure 62:
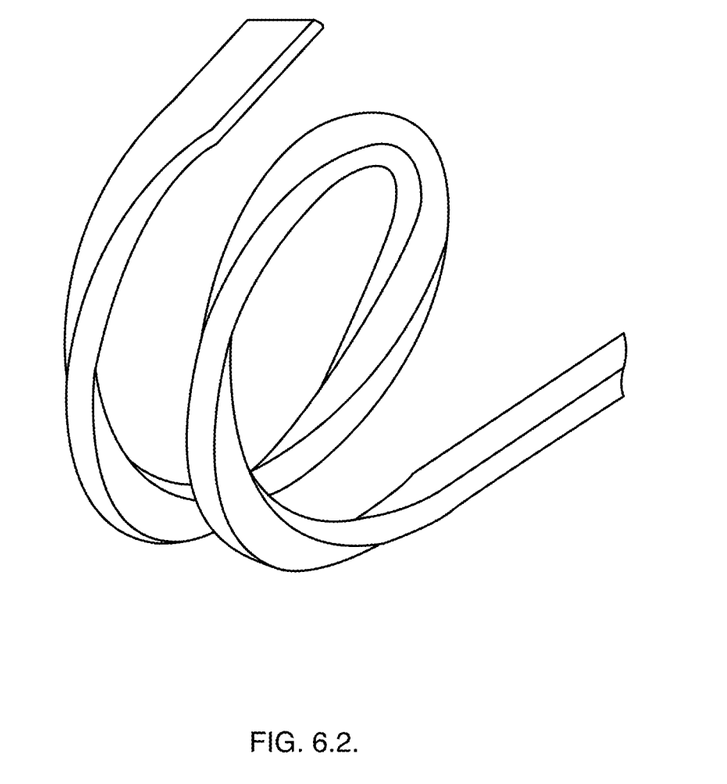
Figure 63:
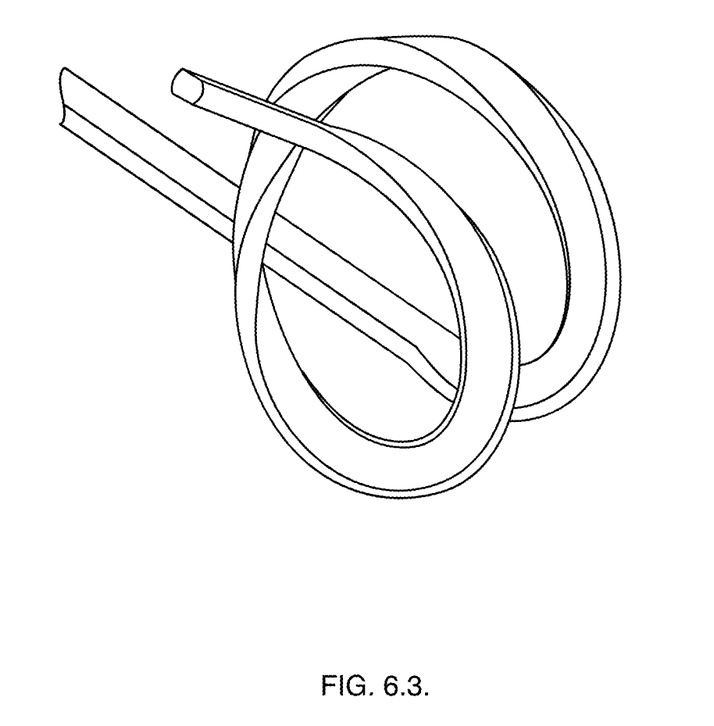

The significant ultrasound feedback should occur a few times over the length of the twisted portion of the coil 44, depending upon the number of twists in the coil. As a result, the twisted coil 44 will produce a more pronounced ultrasonic image than would a non-twisted coil.

In one example, the coil 44 is a 0.020"×0.009" nitinol flat wire. Other wire sizes can be used provided that the wire fits within the needle 28. The coil 44 is shape set in two stages.
1. Shape set a distal end of a straight wire with a twist. Anywhere from ½ a twist/centimeter to more than 4 twists/centimeter may be used.
2. Shape set twisted straight wire into coil shape.

The description of the invention is merely exemplary in nature and variations that do not depart from the gist of the invention are intended to be within the scope of the invention. Such variations are not to be regarded as a departure from the spirit and scope of the invention.

What is claimed is:

1. An electrosurgical device comprising:
a needle configured as a first electrode; and
a flat wire extending through the needle and configured as a second electrode, the flat wire includes four opposing sides two of which have a greater width than other two opposing sides and being movable relative to the needle,
wherein the flat wire is configured to be inserted into a target such that at least a portion of the flat wire attains respective coiled and twisted configurations simultaneously so as to produce a high quality ultrasonic image as compared to a non-twisted coil.

2. The electrosurgical device of claim 1, wherein the flat wire is electrically insulated from the needle.

3. The electrosurgical device of claim 1, wherein the flat wire being adapted to reflect and to produce a stronger ultrasound signal as compared to a standard ANET (Active Needle for Endoscopic Treatment) coil due to the twisted configuration while the flat wire being configured to be inserted into the target.

4. The electrosurgical device of claim 1, wherein the flat wire is made of a shape memory alloy.

5. The electrosurgical device of claim 4, wherein the coiled configuration and the twisted configuration are configured to be attained when the flat wire is heated beyond one or more predefined shape set temperatures.

6. The electrosurgical device of claim 1, wherein at least a portion of the flat wire is twisted when located within the needle.

7. A method comprising:
positioning an applicator in a passageway;
extending a needle through the applicator, the needle being defined as a first electrode;
piercing the needle into a target tissue;
advancing a twisted flat wire through the needle so that a distal portion of the twisted flat wire is piercing into the target tissue while at least a portion of the twisted flat wire attains a coiled configuration so as to produce a high quality ultrasonic image as compared to a non-twisted coil; and
ultrasonically illuminating the twisted flat wire.

8. The method of claim 7 further comprising generating the high quality ultrasonic image based on the ultrasonic illumination of the twisted flat wire.

9. The method of claim 7, wherein the twisted flat wire is electrically insulated from the needle.

10. The method of claim 7, wherein the twisted flat wire reflects an ultrasound signal due to the twisted configuration.

11. The method of claim 7, wherein the twisted flat wire is made of a shape memory alloy.

12. The method of claim 11, wherein the coiled configuration and the twisted configuration are attained when the flat wire is heated beyond one or more predefined shape set temperatures.

13. A system for treating tissue comprising:
an energy source;
a needle connected to the energy source, the needle being defined as a first electrode; and
a flat wire having four opposing sides two of which have a greater width than other two opposing sides, the flat wire extending through the needle and being connected to the energy source while the flat wire is configured to be inserted into a target tissue such that at least a portion of the flat wire attains simultaneously a coiled configuration and a twisted configuration so as to produce a high quality ultrasonic image as compared to a non-twisted coil.

14. The system of claim 13 further comprising an ultrasound device configured to illuminate at least one of the needle or the flat wire and generate the high quality ultrasonic image based on the illumination.

15. The system of claim 14, wherein the flat wire being adapted to reflect an ultrasound signal produced by the ultrasound device as compared to a standard ANET (Active Needle for Endoscopic Treatment) coil due to the twisted configuration while the flat wire being configured to be inserted into the target.

16. The system of claim 13, wherein the flat wire is electrically insulated from the needle.

17. The system of claim 13, wherein the flat wire is made of a shape memory alloy.

18. The system of claim 17, wherein the coiled configuration and the twisted configuration are configured to be attained when the flat wire is heated beyond one or more predefined shape set temperatures.

19. The system of claim 13, wherein at least a portion of the flat wire is twisted when located within the needle.

* * * * *